United States Patent
Okamoto et al.

(10) Patent No.: US 11,771,631 B2
(45) Date of Patent: Oct. 3, 2023

(54) COSMETIC COMPOSITION COMPRISING A SPECIFIC FILLER COMBINATION AND A FILM-FORMING POLYMER TO INCREASE LONG-LASTING EFFECTS

(71) Applicant: L'OREAL, Paris (FR)

(72) Inventors: Mariko Okamoto, Tokyo (JP); Tomofumi Yoshida, Kawasaki (JP); Yuka Kamidoi, Tokyo (JP)

(73) Assignee: L'OREAL, Paris (FR)

( * ) Notice: Subject to any disclaimer, the term of this patent is extended or adjusted under 35 U.S.C. 154(b) by 41 days.

(21) Appl. No.: 16/930,666

(22) Filed: Jul. 16, 2020

(65) Prior Publication Data

US 2021/0007955 A1 Jan. 14, 2021

Related U.S. Application Data

(63) Continuation of application No. 16/061,158, filed as application No. PCT/JP2016/088599 on Dec. 14, 2016, now abandoned.

(30) Foreign Application Priority Data

Dec. 21, 2015 (JP) ................. 2015-248359

(51) Int. Cl.
| | | |
|---|---|---|
| *A61K 8/37* | (2006.01) | |
| *A61K 8/25* | (2006.01) | |
| *A61K 8/26* | (2006.01) | |
| *A61Q 1/02* | (2006.01) | |
| *A61K 8/81* | (2006.01) | |
| *A61K 8/87* | (2006.01) | |
| *A61K 8/06* | (2006.01) | |
| *A61Q 19/00* | (2006.01) | |
| *A61K 8/44* | (2006.01) | |
| *A61K 8/89* | (2006.01) | |

(52) U.S. Cl.
CPC ............... *A61K 8/375* (2013.01); *A61K 8/06* (2013.01); *A61K 8/25* (2013.01); *A61K 8/26* (2013.01); *A61K 8/37* (2013.01); *A61K 8/44* (2013.01); *A61K 8/8152* (2013.01); *A61K 8/87* (2013.01); *A61K 8/89* (2013.01); *A61Q 1/02* (2013.01); *A61Q 19/00* (2013.01)

(58) Field of Classification Search
CPC ... A61K 8/37; A61K 8/25; A61K 8/26; A61K 8/81; A61K 8/87; A61K 8/06; A61K 8/44; A61K 8/89; A61Q 1/02; A61Q 19/00
See application file for complete search history.

(56) References Cited

U.S. PATENT DOCUMENTS

| | | | | |
|---|---|---|---|---|
| 2012/0014888 A1* | 1/2012 | Liu | ............... | A61K 8/02 |
| | | | | 424/59 |
| 2015/0004109 A1* | 1/2015 | Kurkal-Siebert | ...... | A01N 25/30 |
| | | | | 424/60 |
| 2015/0174044 A1 | 6/2015 | Pierre et al. | | |

FOREIGN PATENT DOCUMENTS

| | | | |
|---|---|---|---|
| CN | 104023697 A | | 9/2014 |
| EP | 1269986 | * | 1/2003 |
| FR | 2992182 A1 | | 12/2013 |
| JP | 61-277611 A | | 12/1986 |
| JP | 07-196449 A | | 8/1995 |
| JP | 07-196473 A | | 8/1995 |
| JP | 2002-226328 A | | 8/2002 |
| JP | 2004-210655 A | | 7/2004 |
| JP | 2005-325121 A | | 11/2005 |
| JP | 2005-325122 A | | 11/2005 |
| JP | 2005-325123 A | | 11/2005 |
| JP | 2011-213669 A | | 10/2011 |
| JP | 2013-103885 A | | 5/2013 |
| JP | 2013-542233 A | | 11/2013 |
| JP | 2014-532676 A | | 12/2014 |
| JP | 2014-532678 A | | 12/2014 |
| JP | 2016-145252 A | | 8/2016 |
| JP | 2017-502953 A | | 1/2017 |
| JP | 2017-517500 A | | 6/2017 |
| JP | 2017-190343 A | | 10/2017 |
| KR | 10-2006-0116228 A | | 11/2006 |
| WO | 2012/035512 A1 | | 3/2012 |
| WO | WO 2012/035512 A1 | * | 3/2012 |
| WO | 2013/190102 A2 | | 12/2013 |
| WO | 2013/190112 A1 | | 12/2013 |
| WO | 2014/185539 A1 | | 11/2014 |

OTHER PUBLICATIONS

Sun et al. Journal of Applied Polymer Science, vol. 125, 3532-3536 (2012).*
Crosslinked Alkyl acrylates used in Cosmetics Nov. 17, 2011.*
International Search Report for Application No. PCT/JP2016/088599, dated Mar. 17, 2017.
Korean Office Action for counterpart Application No. 10-2018-7016634, dated May 20, 2019 with English Translation.
Non-Final Office Action for copending U.S. Appl. No. 16/061,158, dated Feb. 21, 2019.

(Continued)

*Primary Examiner* — Shirley V Gembeh
(74) *Attorney, Agent, or Firm* — THE MARBURY LAW GROUP, PLLC

(57) ABSTRACT

The present invention relates to a cosmetic composition for a keratin substance, for example the skin such as that of the face, comprising: (i) at least one moisturizer; (ii) at least one film-forming polymer; and (iii) a combination of the following fillers: (a) hydrophobic silica: (b) perlite; (c) urethane polymer powder; and (d) acrylic polymer powder. "Long-lasting" effects of a cosmetic composition for a keratin substance comprising at least one moisturizer without creating any dry feeling can be achieved by using both a film-forming polymer and a combination of the following fillers: (a) hydrophobic silica: (b) perlite; (c) urethane polymer powder; and (d) acrylic polymer powder.

8 Claims, No Drawings

(56) References Cited

OTHER PUBLICATIONS

Final Office Action for copending U.S. Appl. No. 16/061,158, dated Jul. 30, 2019.
Non-Final Office Action for copending U.S. Appl. No. 16/061,158, dated Nov. 26, 2019.
Final Office Action for copending U.S. Appl. No. 16/061,158, dated Apr. 24, 2020.
Japanese Notice of Allowance for counterpart Application No. 2015-248359, dated Jun. 8, 2020.
Chinese Office Action for counterpart Application No. 201680074111.4, dated Jun. 8, 2020.

* cited by examiner

COSMETIC COMPOSITION COMPRISING A SPECIFIC FILLER COMBINATION AND A FILM-FORMING POLYMER TO INCREASE LONG-LASTING EFFECTS

CROSS REFERENCE TO RELATED APPLICATIONS

This is a continuation application of U.S. application Ser. No. 16/061,158 filed Jun. 11, 2018, which claims priority as a national stage application of PCT/JP2016/088599, filed internationally on Dec. 14, 2016, which claims priority to Japanese Application No. 2015-248359, filed on Dec. 21, 2015, all of which are incorporated by reference herein in their entireties.

TECHNICAL FIELD

The present invention relates to a cosmetic composition for a keratin substance, preferably in liquid emulsion form, in particular a makeup base or a liquid foundation, which provides long-lasting effects without inducing any dry feeling.

BACKGROUND ART

"Long-lasting" effects are one of the key criteria for cosmetic products, in particular in hot and humid countries. A lot of cosmetic products with an emphasis on "long-lasting" effects are commercially available. However, one of the most important drawbacks for these kinds of cosmetic products is to create a dry sensation. Currently, in order to avoid a dry sensation, fatty compounds are added to maintain a moisturizing feeling. For example, WO 2013/190112 discloses a fluid cosmetic skin makeup composition with improved color retention, which comprises at least one continuous oil phase, at least one sebum-pump filler, at least one hydrophobic film-forming polymer, and at least one lipophilic gelling agent.

However, the addition of the fatty compounds leads to a decrease in the "long-lasting" effects. Therefore, it is difficult to develop cosmetics capable of maintaining a balance between the "long-lasting" effects and the moisturizing feeling.

Accordingly, there is still a need for a cosmetic composition for a keratin substance such as the skin, which has "long-lasting" effects while maintaining a moisturizing feeling.

DISCLOSURE OF INVENTION

An objective of the present invention is to provide a cosmetic composition for the skin, preferably in liquid emulsion form, in particular a makeup base or a liquid foundation, which can achieve "long-lasting" effects without creating any dry feeling.

The above objective of the present invention can be achieved by a cosmetic composition for a keratin substance, for example the skin such as that of the face, comprising:
  (i) at least one moisturizer;
  (ii) at least one film-forming polymer; and
  (iii) a combination of the following fillers:
    (a) hydrophobic silica:
    (b) perlite;
    (c) urethane polymer powder; and
    (d) acrylic polymer powder.

The (i) moisturizer may be selected from emollients, humectants and their mixtures.

The (i) moisturizer may be selected from emollients and in particular may be selected from non-volatile oils.

The (i) moisturizer may be selected from ester oils and lipophilic amino acid derivatives.

The amount of the (i) moisturizer in the composition may be from 0.001 to less than 20.0% by weight, preferably from 0.01 to less than 15.0% by weight, and more preferably from 0.05% by weight to 10.0% by weight, relative to the total weight of the composition.

The (ii) film-forming polymer may be silicone resins, preferably selected from MQ resins.

The amount of the (ii) film-forming polymer in the composition may be from 0.01 to less than 20.0% by weight, preferably from 0.1 to less than 15.0% by weight, and more preferably from 1.0% by weight to 10.0% by weight, relative to the total weight of the composition.

The (iii) (a) hydrophobic silica may be silica particles modified at the surface by silylation.

The (iii) (c) urethane polymer powder may be a cross-linked polyurethane powder, preferably hexamethylene diisocyanate (HDI)/trimethylol hexyllactone crosspolymer.

The (iii) (d) acrylic polymer powder may be a crosspolymer or copolymer powder, preferably lauryl methacrylate/glycol dimethacrylate crosspolymer or acrylonitrile/methacrylate/vinylidene chloride copolymer.

The amount of each of the (iii) fillers in the composition may be from 0.001 to less than 10.0% by weight, preferably from 0.01 to less than 8% by weight, and more preferably from 0.05% by weight to 5.0% by weight, relative to the total weight of the composition.

The composition according to the present invention may further comprise at least one UV filter, preferably at least one organic UV filter.

The composition according to the present invention may be a makeup base or a liquid foundation.

The composition according to the present invention may be in the form of an emulsion, in particular of liquid or semi-liquid consistency, of the O/W, W/O or multiple type.

The present invention also relates to a cosmetic process for a keratin substance, for example the skin such as that of the face, comprising the step of: applying the composition according to the present invention onto the keratin substance.

BEST MODE FOR CARRYING OUT THE INVENTION

After diligent research, the inventors have found that "long-lasting" effects of a cosmetic composition for a keratin substance comprising at least one moisturizer without creating any dry feeling can be achieved by using both a film-forming polymer and a combination of the following fillers: (a) hydrophobic silica: (b) perlite; (c) urethane polymer powder; and (d) acrylic polymer powder.

Thus, one aspect of the present invention is a cosmetic composition for a keratin substance, for example the skin such as that of the face, comprising:
  (i) at least one moisturizer;
  (ii) at least one film-forming polymer; and
  (iii) a combination of the following fillers:
    (a) hydrophobic silica:
    (b) perlite;
    (c) urethane polymer powder; and
    (d) acrylic polymer powder.

Another aspect of the present invention is a cosmetic process for a keratin substance, for example the skin such as that of the face, comprising the step of: applying the composition according to the present invention onto the keratin substance.

Hereafter, the composition and process according to the present invention will each be described in a detailed manner.

[Composition]

(Moisturizer)

The composition according to the present invention comprises at least one moisturizer. Two or more moisturizers may be used in combination. Thus, a single type of moisturizer or a combination of different types of moisturizers may be used.

Moisturizers are substances which impart external lubricant behavior, such as to soften and soothe the skin because they promote skin water retention. They may be selected from emollients which are able to remain on the skin surface or in the stratum corneum to act as lubricants, to reduce flaking, and to improve the skin's appearance.

Moisturizers may be also selected from humectants intended to increase the water content of the top layers of skin. This group of ingredients includes primarily hygroscopic agents employed for this specific purpose.

According to a preferred embodiment of the invention, the moisturizer is selected from emollients, humectants and their mixtures.

a) Emollient

In one embodiment, the moisturizer is selected from emollients and more particularly from non-volatile oils. The term "oil" is understood to mean any fatty substance which is in liquid form at ambient temperature (25° C.) and at atmospheric pressure.

Within the meaning of the present invention, the term "non-volatile oil" is understood to mean an oil having a vapor pressure of less than 0.13 Pa (0.01 mmHg).

The non-volatile oils can be chosen in particular from non-volatile hydrocarbon oils, if appropriate fluorinated, and/or non-volatile silicone oils.

As examples of the non-volatile oil suitable for use in the invention, mention may be made of:

hydrocarbon oils of animal origin;

hydrocarbon oils of vegetable origin, such as phytosteryl esters, such as phytosteryl oleate, phytosteryl isostearate and lauroyl/octyldodecyl/phytosteryl glutamate, for example sold under the name Eldew PS203 by Ajinomoto, triglycerides composed of fatty acid esters of glycerol, the fatty acids of which can have varied chain lengths from $C_4$ to $C_{24}$, it being possible for the latter to be linear or branched and saturated or unsaturated; these oils are in particular heptanoic or octanoic triglycerides, wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkinseed oil, cucumber oil, blackcurrant oil, evening primrose oil, millet oil, barley oil, quinoa oil, rye oil, safflower oil, candlenut oil, passionflower oil or musk rose oil; shea butter; or alternatively caprylic/capric acid triglycerides, such as those sold by Stearineries Dubois or those sold under the names Miglyol 810®, 812® and 818® by Dynamit Nobel; or the refined vegetable perhydrosqualene sold under the name Fitoderm by Cognis;

hydrocarbon oils of mineral or synthetic origin, such as, for example, synthetic ethers having from 10 to 40 carbon atoms;

linear or branched hydrocarbons of mineral or synthetic origin, such as liquid petroleum, polydecenes, hydrogenated polyisobutene, such as Parleam, squalane and their mixtures, in particular hydrogenated polyisobutene;

synthetic ester oils, such as oils of formula $R_1COOR_2$ in which $R_1$ represents the residue of a linear or branched fatty acid comprising from 1 to 40 carbon atoms and $R_2$ represents a hydrocarbon chain, in particular a branched hydrocarbon chain, comprising from 1 to 40 carbon atoms, provided that $R_1+R_2$ is ≥10.

As the ester oils, mention may be made of fatty acid esters, such as, for example:

dicaprylyl carbonate (Cetiol CC from Cognis), cetearyl octanoate, esters of isopropyl alcohol, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, such as isostearyl lactate, octyl hydroxystearate, diisopropyl adipate, heptanoates, in particular isostearyl heptanoate, octanoates, decanoates or ricinoleates of alcohols or polyalcohols, such as propylene glycol dioctanoate, cetyl octanoate, tridecyl octanoate, 2-ethylhexyl 4-diheptanoate, 2-ethylhexyl palmitate, alkyl benzoate, polyethylene glycol diheptanoate, propylene glycol di(2-ethylhexanoate) and their mixtures, benzoates of $C_{12}$ to $C_{15}$ alcohols, hexyl laurate, neopentanoic acid esters, such as isodecyl neopentanoate, isotridecyl neopentanoate, isostearyl neopentanoate or octyldodecyl neopentanoate, isononanoic acid esters, such as isononyl isononanoate, isotridecyl isononanoate or octyl isononanoate, or hydroxylated esters, such as isostearyl lactate or diisostearyl malate, polyol esters and pentaerythritol esters, such as monoester or polyester formed between polyol and $C_8$-$C_{40}$ mono fatty acid, which may be formed between a polyol, for example selected from pentaerythritol, erythritol, dipentaerythritol, trimethylolpropane, di-trimethylolpropane, glycerol, diglycerol, polyglycerols and sucrose, and a $C_5$-$C_{40}$, preferably $C_{12}$-$C_{22}$ mono fatty acid, for example optionally-substituted behenic acid and stearic acid such as hydroxystearic acid and isostearic acid, such as dipentaerythirytyl tetrahydroxystearate/tetraisostearate, for example, sold by the company Nisshin Oillio under the name SalacosS 168 EV, esters of dimer diols and of dimer diacids, such as Lusplan DD-DA5® and Lusplan DD-DA7®, sold by Nippon Fine Chemical and described in patent application FR 03 02809.

As examples of the ester oils, mention may also be made of esters formed between aliphatic or aromatic polycarboxylic acid and $C_1$-$C_{10}$ aliphatic or aromatic alcohol.

The aliphatic and aromatic alcohol may comprise from 1 to 10 carbon atoms, for example, 1 to 8, preferably 1 to 6 carbon atoms, and may be selected from alcohol, ROH, in which R is selected from optionally-substituted methyl, ethyl, propyl, isopropyl, butyl, hexyl, ethylhexyl, decyl, isodecyl, and benzyl.

The aliphatic and aromatic polycarboxylic acid may comprise, for example, 3 to 12 carbon atoms, preferably 3 to 10 carbon atoms, more preferably, 3 to 8 carbon atoms, even more preferably 6 or 8 carbon atoms. The aliphatic and aromatic polycarboxylic acid may be a dicarboxylic acid or tricarboxylic acid.

As examples of the dicarboxylic acids, mention may be made of those having the following formula:

$$HOOC-(CH_2)_n-COOH$$

in which n ranges from 1 to 10, preferably from 2 to 8, more preferably, 2, 4, 6 or 8. For example, the dicarboxylic acid may be selected from succinic, adipic and sebacic acids.

The dicarboxylic acid may also be chosen from phthalic acid and its derivatives, for example, butyl benzyl phthalate, dibutyl phthalate, diethylhexyl phthalate, diethyl phthalate and dimethyl phthalate.

As examples of the tricarboxylic acid, mention may be made of those having the following formula:

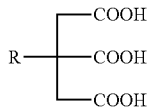

in which R is a hydrocarbon radical, for example H, —OH or —OCOR' wherein R' is alkyl such as alkyl comprising from 1 to 6 carbon atoms. For example, the tricarboxylic acid may be selected from acetylcitric acid and its derivatives.

Among the citrates, mention may be made of tributyl acetylcitrate, triethyl acetylcitrate, triethylhexyl acetylcitrate, trihexyl acetylcitrate, trihexyl butyryl citrate, isodecyl citrate, isopropyl citrate, tributyl citrate and triethylhexyl citrate.

Among adipates, mention may be made of dibutyl adipate and di-2-ethylhexyl adipate.

Among sebacates, mention may be made of dibutyl sebacate, diethylhexyl sebacate, diethyl sebacate and diisopropyl sebacate.

Among succinates, mention may be made of diethylhexyl succinate and diethyl succinate.

Preferably, the ester is formed between a dicarboxylic acid selected from succinic acid, adipic acid and sebacic acid, and an alcohol selected from methanol, ethanol, propanol, isopropanol, butanol, hexanol and ethylhexanol. In particular, the ester may be diisopropyl sebacate, for example, sold by the company Stearinerie Dubois under the name Dub Dis.

As examples of the non-volatile oil, mention may also be made of:
fatty alcohols which are liquid at ambient temperature, comprising a branched and/or unsaturated carbon chain having from 12 to 26 carbon atoms, such as 2-octyldodecanol, isostearyl alcohol, oleyl alcohol, 2-hexyldecanol, 2-butyloctanol and 2-undecylpentadecanol;
higher fatty acids, such as oleic acid, linoleic acid, linolenic acid and their mixtures;
dialkyl carbonates, it being possible for the two alkyl chains to be identical or different, such as dicaprylyl carbonate, sold under the name Cetiol CC® by Cognis;
non-volatile silicone oils, such as, for example, non-volatile polydimethylsiloxanes (PDMSs), polydimethylsiloxanes comprising alkyl or alkoxy groups which are pendent and/or at the ends of the silicone chain, which groups each have from 2 to 24 carbon atoms, phenyl silicones, such as phenyl trimethicones, phenyl dimethicones, phenyl(trimethylsiloxy)diphenylsiloxanes, diphenyl dimethicones, diphenyl(methyldiphenyl)trisiloxanes and (2-phenylethyl)trimethylsiloxysilicates, dimethicones or phenyl trimethicones with a viscosity of less than or equal to 100 cSt, and their mixtures.

As examples of the moisturizer, mention may also be made of lipophilic amino acid derivatives. The lipophilic amino acid derivatives are especially $C_6$-$C_{22}$ N-acylamino acid esters, which can also be defined as the non-volatile oil, in particular the ester oils.

These derivatives are especially those described in patent application EP 1 269 986.

The N-acylamino acid ester(s) are generally of the following formula:

$$R'_1(CO)N(R'_2)CH(R'_3)(CH_2)_n(CO)OR'_4$$

in which:
n is an integer equal to 0, 1 or 2,
$R'_1$ represents a linear or branched $C_5$ to $C_{21}$ alkyl or alkenyl radical,
$R'_2$ represents a hydrogen atom or a $C_1$ to $C_3$ alkyl group,
$R'_3$ represents a radical chosen from the group formed by a hydrogen atom, a methyl group, an ethyl group, a linear or branched $C_3$ or $C_4$ alkyl radical,
$R'_4$ represents a linear or branched $C_1$ to $C_{10}$ alkyl or $C_2$ to $C_{10}$ alkenyl radical, or a sterol residue.

Preferably, the group $R'_1(CO)$— is an acyl group of an acid chosen from the group formed by capric acid, lauric acid, myristic acid, palmitic acid, stearic acid, behenic acid, linoleic acid, linolenic acid, oleic acid, isostearic acid, 2-ethylhexanoic acid, coconut oil fatty acids and palm kernel oil fatty acids. These fatty acids may also contain a hydroxyl group. Even more preferably, it will be lauric acid.

The —N($R'_2$)CH($R'_3$)(CH$_2$)$_n$(CO)— part of the amino acid ester is preferably chosen from the following amino acids: glycine, alanine, valine, leucine, isoleucine, serine, threonine, proline, hydroxyproline, β-alanine, aminobutyric acid, aminocaproic acid, sarcosine, N-methyl-β-alanine.

Even more preferably, it will be sarcosine.

The part of the amino acid esters corresponding to the group $OR'_4$ may be obtained from alcohols chosen from the group formed by methanol, ethanol, propanol, isopropanol, butanol, tert-butanol, isobutanol, 3-methyl-1-butanol, 2-methyl-1-butanol, fusel oil, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, behenyl alcohol, jojoba alcohol, 2-hexadecyl alcohol, 2-octyldodecanol and isostearyl alcohol.

These amino acid esters may be obtained in particular from natural sources of amino acids.

In this case, the amino acids originate from the hydrolysis of natural plant proteins (oat, wheat, soybean, palm or coconut) and then necessarily lead to mixtures of amino acids that subsequently need to be esterified and then N-acylated. The preparation of such amino acids is more particularly described in patent application FR 2 796 550.

The amino acid ester more particularly preferred for its use in the present invention is isopropyl N-lauroylsarcosinate of formula:

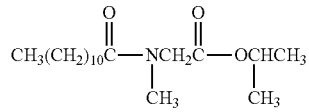

such as the product sold under the name Eldew SL-205 by the company Ajinomoto.

The amino acid esters preferably used for the purposes of the present invention, and the synthesis thereof, are described in patent applications EP 1 044 676 and EP 0 928 608 from the company Ajinomoto Co.

b) Humectants

As examples of humectants, mention may be made of sorbitol, polyhydric alcohols, preferably of $C_2$-$C_8$ and more preferably $C_3$-$C_6$, preferably such as glycerol, propylene glycol, 1,3-butylene glycol, pentylene glycol, hexylene glycol, dipropylene glycol, diethylene glycol and diglycerol, and derivatives and mixtures thereof; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, urea and derivatives thereof; especially Hydrovance (2-hydroxyethylurea) sold by the company National Starch, lactic acids, hyaluronic acid, AHAs, BHAs, sodium pidolate, xylitol, serine, sodium lactate, ectoin and derivatives thereof, chitosan and derivatives thereof, collagen, plankton, an extract of *Imperata cylindra* sold under the name Moist 24 by the company Sederma, acrylic acid homopolymers, for instance Lipidure-HM® from NOF Corporation, beta-glucan and in particular sodium carboxymethyl beta-glucan from Mibelle-AG-Biochemistry, a mixture of passionflower oil, apricot oil, corn oil and rice bran oil sold by the company Nestle under the name NutraLipids®, a C-glycoside derivative such as those described in patent application WO 02/051 828 and in particular C-β-D-xylopyranoside-2-hydroxypropane in the form of a solution containing 30% by weight of active material in a water/propylene glycol mixture (60/40% by weight) such as the product manufactured by the company Chimex under the trade name Mexoryl SBB®, an oil of musk rose sold by the company Nestle, spheres of collagen and of chondroitin sulfate of marine origin (Atelocollagen) sold by the company Engelhard Lyon under the name Marine Filling Spheres, hyaluronic acid spheres such as those sold by the company Engelhard Lyon, arginine, argan oil, and mixtures thereof.

The amount of the moisturizer in the composition may be from 0.001 to less than 20.0% by weight, preferably from 0.01 to less than 15.0% by weight, and more preferably from 0.05% by weight to 10.0% by weight, relative to the total weight of the composition.

(Film-Forming Polymer)

The composition according to the present invention comprises at least one film-forming polymer. Two or more film-forming polymers may be used in combination. Thus, a single type of film-forming polymer or a combination of different types of film-forming polymers may be used.

For the purposes of the present invention, the term "polymer" means a compound corresponding to the repetition of one or more units (these units being derived from compounds known as monomers). This or these units(s) are repeated at least twice and preferably at least three times.

The term "film-forming polymer" means a polymer that is capable of forming, by itself or in the presence of an auxiliary film-forming agent, a macroscopically continuous film that adheres to a support, especially to keratin materials, preferably a cohesive film, and better still a film whose cohesion and mechanical properties are such that the said film may be isolable and manipulable in isolation, for example, when the said film is prepared by pouring onto a non-stick surface, for instance, a Teflon-coated or silicone-coated surface.

According to one embodiment of the present invention, the film-forming polymer may be selected from the group comprising:
  film-forming polymers that are soluble in an organic solvent medium, in particular liposoluble polymers; this means that the polymer is soluble or miscible in the organic medium and will form a single homogeneous phase when it is incorporated into the medium;
  film-forming polymers that are dispersible in an organic solvent medium; this means that the polymer forms an insoluble phase in the organic medium, the polymer remaining stable and/or compatible once incorporated into this medium. In particular, such polymers may be in the form of non-aqueous dispersions of polymer particles, preferably dispersions in silicone-based or hydrocarbon-based oils; in one embodiment, the non-aqueous dispersions of polymer comprise polymer particles stabilized on their surface with at least one stabilizer; these non-aqueous dispersions are often referred to as "NADs"; and
  film-forming polymers in the form of aqueous dispersions of polymer particles; this means that the polymer forms an insoluble phase in water, the polymer remaining stable and/or compatible once incorporated into the water, the polymer particles possibly being stabilized at their surface with at least one stabilizer. These polymer particles are often referred to as "lattices"; in this case, the composition must comprise an aqueous phase.

The amount of the film-forming polymer in the composition may be from 0.01 to less than 20.0% by weight, preferably from 0.1 to less than 15.0% by weight, and more preferably from 1.0% by weight to 10.0% by weight, relative to the total weight of the composition.

Preferably, the film-forming polymer is selected from the group consisting of polyamide-silicone block polymers, block ethylenic polymers, vinyl polymers comprising at least one carboxiloxane dendrimer derivative, copolymers comprising carboxylate groups and polydimethylsilixane groups, silicone resins, lipodispersible polymers in the form of a non-aqueous dispersion of polymer particles, olefin copolymers selected from amorphous olefin copolymers and olefin copolymers with controlled and moderate crystallization, hydrocarbon-based resins having a number-average molecular weight of less than or equal to 10,000 g/ml, and a mixture thereof, more preferably from silicone resins.

The film-forming silicone resin may be any silicone resin which has film-forming properties.

According to one embodiment of the present invention, the film-forming silicone resin may be selected from silsesquioxane, siloxysilicate and a resin obtained by hydroxysilylation.

The nomenclature of the silicone resin is known in the art under the name of "MDTQ" nomenclature, by which a silicone resin is described according to the various repeating siloxane monomer moieties which constitute the polymer. Each letter of "MDTQ" corresponds to a different type of moiety.

The symbol "M" corresponds to the monofunctional moiety $(CH_3)_3SiO_{1/2}$. This moiety is regarded as monofunctional because the silicon atom shares only one oxygen for the formation of the chain. The "M" moiety can be represented by the following structure:

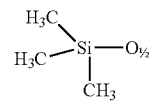

At least one of the methyl groups can be replaced so as, for example, to produce a moiety with the following formula: $[R(CH_3)_2]SiO_{1/2}$, such as represented by the following structure:

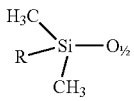

in which R is other than a methyl group.

The symbol "D" corresponds to the difunctional moiety $(CH_3)SiO_{2/2}$ in which two of the available bonds on the silicon atom are used to bond with oxygen for the formation of the polymer chain. The "D" moiety, which is the essential component element of the dimethicone oils, can be represented by the following formula:

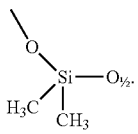

The symbol "T" corresponds to the trifunctional moiety $(CH_3)SiO_{3/2}$, in which three of the available bonds on the silicon atom are used to bond with oxygen for the formation of the polymer chain. The "T" moiety can be represented by the following structure:

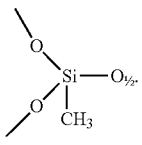

As in the "M" moiety, any one of the methyl groups can be replaced in "D" or "T" by an R group which is other than methyl.

Finally, the symbol "Q" corresponds to a quadrifunctional moiety $SiO_{4/2}$, in which all four available bonds on the silicon atom are used to bond with oxygen for the formation of the polymer chain. The "Q" moiety can be represented by the following structure:

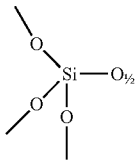

As described above, in one embodiment of the present invention, the film-forming silicone resin may be selected from the siloxysilicate, silsesquioxane and a resin obtained by hydroxysililation. Any siloxysilicate, silsesquioxane or resin obtained by hydroxysilylation, which acts as a film-forming agent, can be used in the composition of the present invention. The film-forming silicone resin preferably is crosslinked.

According to one embodiment of the present invention, the film-forming silicone resin may be selected from substituted siloxysilicate, silsesquioxane and resin obtained by hydroxysilylation. A substituted siloxysilicate or a substituted silsesquioxane may be, for example, a siloxysilicate or a silsesquioxane in which a methyl group has been replaced by a longer carbon chain, such as an ethane, propane or butane chain. The carbon chain may be saturated or nonsaturated.

According to one embodiment of the present invention, the film-forming silicone resin may be selected from siloxysilicate, such as MQ resins represented by the following formula:

$[(CH_3)_3SiO_{1/2}]_x(SiO_{4/2})_y$ (MQ moieties)

in which x and y may have values ranging from 20 to 100, preferably 50 to 80.

According to another embodiment of the present invention, siloxysilicate may be selected from all the combinations of M and of Q moieties such as, for example, $[(R)_3Si]_x(SiO_{4/2})_y$, in which R is selected from a methyl group and a longer carbon chain.

According to another embodiment of the present invention, the film-forming silicone resin may be selected from silsesquioxane represented by the following formula:

$(CH_3SiO_{3/2})_x$ (T moieties), in which x has a value which can range up to several thousands and the $CH_3$ can be replaced by an R, such as described hereinabove for the T moieties.

Most preferably, the film-forming silicone resin is trimethylsiloxysilicate, for example, sold by the company Momentive Performance Materials under the name SR 1000 MQ Resin.

(Filler)

The composition according to the present invention comprises a filler combination of (a) hydrophobic silica, (b) perlite, (c) urethane polymer powder, and (d) acrylic polymer powder.

The term "fillers" mean colorless or white, mineral or synthetic particles of any shape, which are insoluble in the medium of the composition, irrespective of the temperature at which the composition is manufactured.

The amount of each of the (a) to (d) fillers in the composition may be from 0.001 to less than 10.0% by weight, preferably from 0.01 to less than 8% by weight, and more preferably from 0.05% by weight to 5.0% by weight, relative to the total weight of the composition.

(a) Hydrophobic Silica

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups, for example trimethylsilyl groups. The silica may also be treated with dimethyldichlorosilane or alternatively with a polydimethylsiloxane.

As examples of commercial references of silica suitable for the present invention, mention may be made of the silicas sold under the references Silica Beads SB 150 and SB 700 from Miyoshi, having a mean size of 5 microns, and the Sunspheres H33, H51 and H53 from Asahi Glass, having respective sizes of about 3, 5 and 5 microns.

As the hydrophobic silica, mention may also be made of hydrophobic fumed silica. The hydrophobic fumed silicas can be obtained by modification of the surface of the silica by means of a chemical reaction that creates a decrease in the number of silanol groups, it being possible for these groups to be in particular substituted with hydrophobic groups.

The hydrophobic groups may be:
trimethylsiloxyl groups, which are in particular obtained by treatment of fumed silica in the presence of hexamethyldisilazane. Silicas treated in this way are called "Silica silylate" according to the CTFA (6th edition, 1995). They are, for example, sold under the references "AEROSIL R202®", "AEROSIL R805®" and "AEROSIL R812®" by the company Degussa, and "CAB-O-SIL TS-530®" by the company Cabot.;
dimethylsilyloxyl or polydimethylsiloxane groups, which are in particular obtained by treatment of fumed silica in the presence of polydimethylsiloxane or of dimethyldichlorosilane. Silicas treated in this way are called "Silica dimethyl silylate" according to the CTFA (6th edition, 1995). They are, for example, sold under the references "AEROSIL R972®" and "AEROSIL R974®" by the company Degussa, and "CAB-O-SIL TS-610®" and "CAB-O-SIL TS-720®" by the company Cabot.

As preferred examples of the hydrophobic silica, mention may be made of
the aerogel sold under the name VM-2260 (INCI name: Silica silylate) by the company Dow Corning, the particles of which have a mean size of approximately 1000 microns and a specific surface area per unit of mass ranging from 600 to 800 $m^2/g$,
the aerogels sold by the company Cabot under the references Aerogel TLD 201, Aerogel OGD 201, Aerogel TLD 203, Enova® Aerogel MT 1100 and Enova Aerogel MT 1200,
the aerogel sold under the name VM-2270 (INCI name: Silica silylate), by the company Dow Corning, the particles of which have an average size ranging from 5-15 microns and a specific surface area per unit of mass ranging from 600 to 800 $m^2/g$.

As regards the preparation of hydrophobic silica aerogel particles, reference may be made to the document U.S. Pat. No. 7,470,725.

Most preferably, the hydrophobic silica is silica silylate, for example, sold by the company Dow Corning under the name Dow Corning VM-2270 Aerogel Fine Particles.

(b) Perlite

Perlite is generally obtained from natural glass of volcanic origin, of light-grey or glossy black color, resulting from the rapid cooling of lava, and which is in the form of small particles resembling pearls. When heated above 800° C., perlite has the particular feature of losing the water it contains and of adopting a porous expanded form (representing from four to twenty times its initial volume), enabling it to absorb large amounts of liquid, in particular oil and water. It then has a white color.

Perlite, which is of mineral origin, is directly extracted from the ground and then finely ground to obtain a very fine white powder: perlite powder or perlite particles.

Perlite particles are thus particles of amorphous mineral materials, which are advantageously expanded, derived from at least one volcanic rock.

These particles may comprise at least two elements chosen from silicon, aluminum and magnesium.

More particularly, these mineral materials may be obtained by thermal expansion of a volcanic or "effusive" rock comprising from 1% to 10% by weight of water and preferably 1% to 5% by weight of water and less than 10% by weight of crystalline rock relative to the total weight of the rock composition and preferably followed by grinding. The temperature of the expansion process may range from 700 to 1500° C. and preferably from 800 to 1100° C.

The expansion process described in U.S. Pat. No. 5,002,698 may especially be used.

Volcanic or "effusive" rocks are generally produced by the rapid cooling of liquid magma in contact with air or water (quenching phenomenon giving a hyaline rock). The volcanic rocks that may be used according to the present invention may be selected from those defined according to the Streckeisen classification (1974). Among these volcanic rocks, mention may especially be made of trachytes, latites, andesites, basalts, rhyolites and dacites.

For example, the perlite particles are aluminosilicates of volcanic origin. They advantageously have the following composition:
70.0-75.0% by weight of silica ($SiO_2$);
12.0-15.0% by weight of aluminum oxide ($Al_2O_3$);
3.0-5.0% of sodium oxide ($Na_2O$);
3.0-5.0% of potassium oxide ($K_2O$);
0.5-2% of iron oxide ($Fe_2O_3$);
0.2-0.7% of magnesium oxide (MgO);
0.5-1.5% of calcium oxide (CaO); and
0.05-0.15% of titanium oxide ($TiO_2$).

Preferably, the composition according to the present invention comprises perlite sold by the company Miyoshi Kasei under the name Perlite-M SZ12.

(c) Urethane Polymer Powder

The term "urethane polymer powder" means fillers consisting of a material at least partly of polyurethane type.

According to one embodiment of the present invention, the polyurethane material may advantageously be in cross-linked form.

According to one embodiment of the present invention, the urethane polymer powder may generally be substantially spherical. The term "spherical" means an essentially spherical shape, especially in the form of beads, preferably of a number-average size ranging from 1 to 15 µm, including 4, 5, 6, 7, 8, 9, 10, 11, 12, 13, 14, 15, 16, 17, 18, and 19 µm, and all subranges and values between stated values. The term "number-average size" denotes the dimension given by the random particle size distribution to half the population, known as D50.

For example, the urethane polymer powder may comprise a copolymer. Said copolymer may comprise trimethylol hexyllactone, in particular a hexamethylene diisocyanate (HDI)/trimethylol hexyllactone crosspolymer. As examples of the copolymer, mention may be made of urethane polymer powder sold by the company Toshiki under the name Plastic Powder D-400® or Plastic Powder D-800® or sold by the company Shiki under the name Plastic Powder CS-400®.

Most preferably, as the urethane polymer powder, the composition according to the present invention comprises hexamethylene diisocyanate (HDI)/trimethylol hexyllactone crosspolymer, for example, sold by the company Toshiki Pigment under the name Plastic Powder D 400.

(d) Acrylic Polymer Powder

The term "acrylic polymer powder" means fillers obtained by polymerization of an acrylate and/or methacrylate monomer(s) optionally-substituted with $C_1$-$C_{20}$ alkyl, in the form of a homopolymer or of a copolymer.

As examples of the acrylic polymer powder, mention may be made of powder of polymethyl methacrylate, of polymethyl methacrylate/ethylene glycol dimethacrylate, of polyallyl methacrylate/ethylene glycol dimethacrylate, of lauryl methacrylate/ethylene glycol dimethacrylate, and of acrylonitrile/methacrylate/vinylidene chloride copolymer.

The acrylic polymer powder is generally preferably in the form of white-colored, hollow or solid, spherical particles of which the number-average size is generally preferably on the micrometer scale, and in particular ranges from 3 to 20 µm, and generally ranges from 7 to 15 µm, including 4, 5, 6, 7, 8, 9, 10, 11, 12, 13, 14, 15, 16, 17, 18, and 19 µm, and all subranges and values between stated values.

As examples of the acrylic polymer powder, mention may be made of:

powder of crosslinked polymethyl methacrylate, for instance "Covabead LH85" sold by the company LC Wackherr, or of noncrosslinked polymethyl methacrylate, such as SJ Touch 1 sold by the company Nihon Junyaku;

powder of methyl methacrylate/butyl acrylate copolymer sold under the name Sepipress M by the company Seppic;

powder of methyl acrylate/ethylene copolymer sold under the name EMAA by the company Kobo Products Inc.;

powder of methyl methacrylate/ethylene glycol dimethacrylate crosslinked copolymer sold under the name Ganzpearl GMP 0820 by the company Ganz Chemical, under the name Techpolymer MBP-8 by the company Sekisui Plastics, or else under the name SUNPMMA-S by the company Sunjin Chemical;

powder of polymethyl methacrylate/ethylene glycol dimethacrylate, for example "Dow Corning 5640 Microsponge Skin Oil Adsorber" sold by the company Dow Corning;

powder of methyl methacrylate/ethylene glycol dimethacrylate crosslinked copolymer sold under the name Ganzpearl PM 030 by the company Ganz Chemical;

powder of polyallyl methacrylate/ethylene glycol dimethacrylate, for instance "Poly-Pore L200" or "Poly-Pore E200" sold by the company Amcol, powder of lauryl methacrylate/ethylene glycol dimethacrylate copolymer, for instance "Polytrap 6603" sold by the company Dow Corning;

powder of acrylonitrile/methacrylate/vinylidene chloride copolymer sold under the name Expancel by the company Expancel under the references 551 DE 50, 551 DE 20, 551 DE 12, 551 DE 80, and 461 DE 50.

Preferably, the acrylic polymer powder is lauryl methacrylate/ethylene glycol dimethacrylate crosspolymer, for example, sold by the company Amcol Health & Beauty Solutions under the name Polytrap 6603 Adsorber, and/or acrylonitrile/methacrylate/vinylidine chloride copolymer, for example, sold by the company Akzo Nobel under the name Expancel 551 DE D42.

(e) Other Fillers

The composition according to the present invention may comprise at least one additional filler other than (a) hydrophobic silica, (b) perlite, (c) urethane polymer powder, and (d) acrylic polymer powder.

The additional filler may be selected from fillers such as:

elastomeric crosslinked organopolysiloxane spherical powders, described especially in document JP-A-02 243 612, such as those sold under the name Trefil Powder E-506C by the company Dow Corning;

the camauba wax microbeads sold under the name Microcare 350® by the company Micro Powders and the paraffin wax microbeads sold under the name Microease 114S® by the company Micro Powders;

metal soaps in powder form, for example metal soaps of fatty acids containing from 12 to 22 carbon atoms and in particular those containing from 12 to 18 carbon atoms wherein the metal of the metal soap may especially be zinc or magnesium and the fatty acid may be selected from lauric acid, myristic acid, stearic acid and palmitic acid, preferably zinc laurate, magnesium stearate, magnesium myristate and zinc stearate, and mixtures thereof;

talcs or hydrated magnesium silicates, especially in the form of particles generally less than 40 µm in size;

micas or aluminosilicates of varied composition that are especially in the form of flakes from 2 to 200 µm and preferably 5 to 70 µm in size and from 0.1 to 5 µm and preferably 0.2 to 3 µm in thickness, these micas possibly being of natural origin (for example muscovite, margarite, roscoelite, lepidolite or biotite) or of synthetic origin; clays such as sericites, which belong to the same chemical and crystalline class as muscovite;

kaolin or hydrated aluminum silicate, which is especially in the form of particles of isotropic forms generally less than 30 µm in size;

boron nitrides;

powders of tetrafluoroethylene polymers, such as Ceridust 9205 F from the company Clariant;

precipitated calcium carbonate, especially in the form of particles greater than 10 µm in size;

magnesium carbonate and magnesium hydrogen carbonate;

hydroxyapatite;

powders of non-expanded synthetic polymers, such as polyethylene, polyesters (for example polyethylene isophthalate or terephthalate) and polyamides (for example Nylon), in the form of particles less than 50 µm in size;

powders of spheronized, crosslinked or non-crosslinked synthetic polymers, for instance polyamide powders such as poly-β-alanine powder or Nylon powder, for example Orgasol powder from the company Atochem, polyacrylic acid or polymethacrylic acid powder, powders of polystyrene crosslinked with divinylbenzene, and silicone resin powders; and bismuth oxychloride powders;

powder of organic materials of natural origin, for instance starches, especially corn starch, wheat starch or rice starch; and mixtures thereof.

According to one embodiment of the present invention, the composition according to the present invention may comprise polyamide powder, for example that listed under the CTFA name of "Nylon 12" or "Nylon 6". A mixture of polyamide powder and, for example, a mixture of Nylon-6 and Nylon-12 may be used.

The polyamide powder includes that sold by the company Toray Industries under the name SP-500.

According to one embodiment of the present invention, the amount of the additional filler in the composition may be from 0.01 to less than 10.0% by weight, and preferably from 0.1 to less than 5.0% by weight, relative to the total weight of the composition.

(UV Filter)

The composition according to the present invention may include at least one UV filter. If two or more UV filters are used, they may be the same or different.

The UV filter may be solid or liquid, preferably liquid. The terms "solid" and "liquid" mean solid and liquid, respectively, at 25° C. under 1 atm. The UV filter may be made from at least one organic or inorganic material, preferably at least one organic material. Thus, the UV filter is preferably an organic UV filter.

The organic UV filter may be selected from the group consisting of anthranilic derivatives; dibenzoylmethane derivatives; cinnamic derivatives; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazoline derivatives; bis-benzoazolyl derivatives; p-aminobenzoic acid (PABA) and derivatives thereof; benzoxazole derivatives; screening polymers and screening silicones; dimers derived from α-alkylstyrene; 4,4-diarylbutadienes; octocrylene and derivatives thereof, guaiazulene and derivatives thereof, rutin and derivatives thereof, flavonoids, biflavonoids, oryzanol and derivatives thereof, quinic acid and derivatives thereof, phenols, retinol, cysteine, aromatic amino acids, peptides having an aromatic amino acid residue, and mixtures thereof.

Mention may be made, as examples of the organic UV filter, of those denoted below under their INCI names, and mixtures thereof.

Anthranilic derivatives: Menthyl anthranilate, marketed under the trademark "Neo Heliopan MA" by Haarmann and Reimer.

Dibenzoylmethane derivatives: Butyl methoxydibenzoylmethane, marketed in particular under the trademark "Parsol 1789" by Hoffmann-La Roche; and isopropyl dibenzoylmethane.

Cinnamic derivatives: Ethylhexyl methoxycinnamate, marketed in particular under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic derivatives: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer.

Camphor derivatives, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylaniidomethyl benzylidene camphor, manufactured under the trademark "Mexoryl SW" by Chimex.

Benzophenone derivatives: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; benzophenone-12, and n-hexyl 2-(4-diethylamino-2-hydroxybenzoyl)benzoate.

β,β-Diphenylacrylate derivatives: Octocrylene, marketed in particular under the trademark "Uvinul N539" by BASF; and Etocrylene, marketed in particular under the trademark "Uvinul N35" by BASF.

Triazine derivatives: diethylhexyl butamido triazone, marketed under the trademark "Uvasorb HEB" by Sigma 3V; 2,4,6-tris(dineopentyl 4'-aminobenzalmalonate)-s-triazine.

Benzotriazole derivatives, in particular, phenylbenzotriazole derivatives: 2-(2H-benzotriazole-2-yl)-6-dodecyl-4-methylphenol, branched and linear; and those described in U.S. Pat. No. 5,240,975.

Benzalmalonate derivatives: Dineopentyl 4'-methoxybenzalmalonate, and polyorganosiloxane comprising benzalmalonate functional groups, such as polysilicone-15, marketed under the trademark "Parsol SLX" by Hoffmann-LaRoche.

Benzimidazole derivatives, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer.

Imidazoline derivatives: Ethylhexyl dimethoxybenzylidene dioxoimidazoline propionate.

Bis-benzoazolyl derivatives: The derivatives as described in EP-669,323 and U.S. Pat. No. 2,463,264.

Para-aminobenzoic acid and derivatives thereof: PABA (p-aminobenzoic acid), ethyl PABA, Ethyl dihydroxypropyl PABA, pentyl dimethyl PABA, ethylhexyl dimethyl PABA, marketed in particular under the trademark "Escalol 507" by ISP, glyceryl PABA, and PEG-25 PABA, marketed under the trademark "Uvinul P25" by BASF.

Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184 and EP-893,119, and Drometrizole trisiloxane, marketed under the trademark "Silatrizole" by Rhodia Chimie or "Mexoryl XL" by L'Oreal, as represented below.

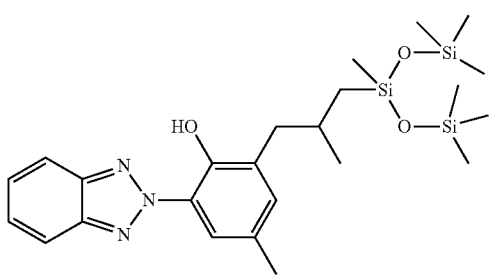 [SMILES: Cc1cc(CC(C)C[Si](C)(O[Si](C)(C)C)O[Si](C)(C)C)c(O)c(-n2nc3ccccc3n2)c1]

Benzoxazole derivatives:
2,4-bis[5-1 (dimethylpropyl)benzoxazol-2-yl-(4-phenyl) imino]-6-(2-ethylhexy)imino-1,3,5-triazine, marketed under the trademark of Uvasorb K2A by Sigma 3V.

Screening polymers and screening silicones: The silicones described in WO 93/04665.

Dimers derived from α-alkylstyrene: The dimers described in DE-19855649.

4,4-Diarylbutadiene derivatives:
1,1-dicarboxy(2,2'-dimethylpropyl)-4,4-diphenylbutadiene.

Guaiazulene and derivatives thereof: Guaiazulene and sodium guaiazulene sulfonate.

Rutin and derivatives thereof: Rutin and glucosylrutin.

Flavonoids: Robustin (isoflavonoid), genistein (flavonoid), tectochrysin (flavonoid), and hispidone (flavonoid).

Biflavonoids: Lanceolatin A, lanceolatin B, and hypnumbiflavonoid A.

Oryzanol and derivatives thereof: γ-oryzanol.

Quinic acid and derivatives thereof: Quinic acid.

Phenols: Phenol.

Retinols: Retinol.

Cysteines: L-cysteine.

Peptides having an aromatic amino acid residue: Peptides having tryptophan, tyrosine or phenylalanine.

The preferred organic UV filter may be selected from: butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, methylene bis-benzotriazolyl tetramethylbutylphenol, polysilicone-15, dineopentyl 4'-methoxybenzalmalonate, 1,1-dicarboxy(2,2'-dimethylpropyl)-4,4-diphenylbutadiene, 2,4-bis[5-1(dimethylpropyl)benzoxazol-2-yl-(4-phenyl)imino]-6-(2-ethylhexyl)imino-1,3,5-tri azine, and their mixtures. A more preferable organic UV filter is butyl methoxydibenzoylmethane (Avobenzone).

In a preferred embodiment, the UV filter is an organic liquid UV filter.

The material of the organic liquid UV filter is not limited as long as it is organic. If two or more organic liquid UV filters are used, the material(s) of the organic liquid UV filters may be the same as or different from each other.

Amongst the organic liquid UV filter, we can mention:

Cinnamic derivatives: Ethylhexyl methoxycinnamate, marketed in particular under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic derivatives: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer.

β,β-Diphenylacrylate derivatives: Octocrylene, marketed in particular under the trademark "Uvinul N539" by BASF; and Etocrylene, marketed in particular under the trademark "Uvinul N35" by BASF.

Polyorganosiloxane comprising benzalmalonate functional groups, such as polysilicone-15, marketed under the trademark "Parsol SLX" by Hoffmann-LaRoche.

The preferred organic liquid UV filter(s) may be selected from methoxycinnamate, homosalate, ethylhexyl salicylate, ethylhexyl triazone, octocrylene, drometrizole trisiloxane, n-hexyl 2-(4-diethylamino-2-hydroxybenzoyl)benzoate, terephthalylidene dicamphor sulfonic acid, and bis-ethylhexyloxyphenol methoxyphenyl triazine.

The UV filter(s) may be present in the composition used for the present invention in a content ranging from 0.1 to 40% by weight, preferably ranging from 1 to 20% by weight, and more preferably from 3 to 10% by weight, relative to the total weight of the composition.

(Additive)

According to a particular embodiment of the present invention, the composition according to the present invention further comprises at least one compound selected from water, hydrophilic solvents, lipophilic solvents, volatile oils, and mixtures thereof.

As the hydrophilic solvents, mention may be made of monoalcohol, such as ethanol, propanol, butanol, isopropanol or isobutanol; polyethylene glycols; polyols, such as propylene glycol, isoprene glycol, butylene glycol, glycerol or sorbitol; mono- or dialkyl derivatives of isosorbide, such as dimethyl isosorbide; glycol ethers, such as diethylene glycol monomethyl or monoethyl ether, and propylene glycol ethers, such as dipropylene glycol methyl ether.

The composition according to the present invention may also comprise any additive usually used in the field under consideration, chosen, for example, from gums, anionic, cationic, amphoteric, or nonionic surfactants, silicone surfactants, resins, thickeners, structuring agents such as waxes, dispersants, antioxidants, essential oils, preserving agents, fragrances, neutralizers, antiseptics, cosmetic active agents, such as vitamins, emollients, or pigments, and mixtures thereof.

As the thickeners, mention may be made of polymeric or mineral thickeners, preferably selected from hydrophilic thickeners, lipophilic thickeners, or a mixture thereof. More preferably the thickener is selected from polysaccharide biopolymers, lipophilic clays, hydrophobic silicas, or a mixture thereof, even more preferably the thickener is chosen from xanthan gum, disteardimonium hectorite, silica silylate, or a mixture thereof. Most preferably, the thickeners are disteardimonium hectorite.

As the pigments, mention may be made of white or colored, mineral or organic particles that are insoluble in an aqueous solution, for example titanium oxide, zirconium oxide or cerium oxide, and also zinc oxide, iron oxide or chromium oxide, ferric blue, manganese violet, ultramarine blue, and chromium hydrate.

It is a matter of routine operations for a person skilled in the art to adjust the nature and amount of the additives present in the cosmetic compositions according to the present invention such that the desired cosmetic properties and stability properties thereof are not thereby affected.

The cosmetic composition according to the present invention may be in the form of a skin makeup product, in particular a makeup base, a foundation, a hot-cast foundation product, a body makeup product, a concealer, an eyeshadow, a lipstick, or a body deodorant. In a particular embodiment, the cosmetic composition may be a makeup base or a liquid foundation.

The composition according to the present invention may be in any of the formulation forms conventionally used, preferably in the form of an emulsion, in particular of liquid or semi-liquid consistency, of the O/W, W/O or multiple type.

According to one embodiment of the present invention, the present invention also relates to a method for improving "long-lasting" effects without creating any dry feeling, characterized by adding at least one film-forming polymer and a combination of the following fillers: (a) hydrophobic silica, (b) perlite, (c) urethane polymer powder, and (d) acrylic polymer powder to a cosmetic composition for a keratin substance, for example the skin such as that of the face, in particular a makeup base or a liquid foundation, the cosmetic composition comprising at least one moisturizer.

According to a particular embodiment of the present invention, the present invention relates to use of at least one film-forming polymer and a combination of the following fillers: (a) hydrophobic silica, (b) perlite, (c) urethane polymer powder, and (d) acrylic polymer powder for providing "long-lasting" effects with a cosmetic composition for a keratin substance comprising at least one moisturizer without creating any dry feeling.

[Cosmetic Process]

The present invention also relates to cosmetic process for a keratin substance, for example the skin such as that of the face, comprising the step of: applying the composition according to the present invention onto the keratin substance.

Simultaneous use of a film-forming polymer and a combination of the following fillers: (a) hydrophobic silica, (b) perlite, (c) urethane polymer powder, and (d) acrylic polymer powder can improve "long-lasting" effects for a cosmetic composition for a keratin substance comprising a moisturizer without creating any dry feeling.

EXAMPLES

The present invention will be described in a more detailed manner by way of examples. However, these examples should not be construed as limiting the scope of the present invention.

Makeup Base Example

Example 1 and Comparative Examples 1-6

The makeup base compositions according to Example 1 and Comparative Examples 1-6 shown in Table 1 were prepared by mixing the ingredients shown in Table 1 as follows: (1) adding phases A1 and A2 to a main beaker; (2) adding phase A3 and dissolving it completely; (3) adding phase A4 and dispersing it homogeneously; (4) adding phase B and dispersing it homogenously; (5) adding phase C and dispersing it homogenously; (6) adding phase D and emulsifying the resultant mixture; and (7) adding phase E and dispersing it homogenously. The numerical values for the amounts of the ingredients shown in Table 1, are all based on "% by weight" as active raw materials.

TABLE 1

| | | Example | Comparative Example | | | | | |
|---|---|---|---|---|---|---|---|---|
| Phase | Ingredient | 1 | 1 | 2 | 3 | 4 | 5 | 6 |
| A1 | PEG-10 Dimethicone | 3.00 | 3.00 | 3.00 | 3.00 | 3.00 | 3.00 | 3.00 |
| | BIS-PEG/PPG-14/14 Dimethicone (and) dimethicone | 1.00 | 1.00 | 1.00 | 1.00 | 1.00 | 1.00 | 1.00 |
| | Dimethicone | qs 100 | qs 100 | qs 100 | qs 100 | qs 100 | qs 100 | qs 100 |
| A2 | Dipentaerythrityl tetrahydroxystearate/tetraisostearate (SalacosS 168 EV by Nisshin Oillio) | 0.10 | — | 0.10 | 0.30 | 0.30 | 0.30 | 0.30 |
| | Ethylhexyl methoxycinnamate (Uvinul MC 80 by BASF) | 4.00 | — | 4.00 | 4.00 | 4.00 | 4.00 | 4.00 |
| A3 | Trimethylsiloxysilicate (SR 1000 MQ Resin by Momentive Performance Materials) | 5.00 | 5.00 | — | 5.00 | 5.00 | 5.00 | 5.00 |
| A4 | Disteardimonium hectorite | 0.50 | 0.50 | 0.50 | 0.50 | 0.50 | 0.50 | 0.50 |
| B | Silica silylate(Dow Corning VM-2270 Aerogel Fine Particles) | 0.10 | 0.10 | 0.10 | — | 0.10 | 0.10 | 0.10 |
| | Lauryl methcrylate/glycol dimethacrylate crosspolymer (Polytrap 6603 Adsorber by Amcol Health & Beauty Solutions) | 1.00 | 1.00 | 1.00 | 1.00 | — | 1.00 | 1.00 |
| | Perlite (Perlite-M SZ12 by Miyoshi Kasei) | 1.00 | 1.00 | 1.00 | 1.00 | 1.00 | — | 1.00 |
| | HDI/trimethylol hexyllactone crosspolymer (Plastic Powder D 400 by Toshiki Pigment) | 1.00 | 1.00 | 1.00 | 1.00 | 1.00 | 1.00 | — |
| C | Titanium dioxide (and) aluminum hydroxide (and) dimethicone (and) hydrogen dimethicone | 3.00 | 3.00 | 3.00 | 3.00 | 3.00 | 3.00 | 3.00 |
| | Iron oxides (and) disodium stearoyl glutamate (and) aluminum hydroxide (NAI-C3 3-9001-10/Miyoshi Kasei) | 0.03 | 0.03 | 0.03 | 0.03 | 0.03 | 0.03 | 0.03 |

TABLE 1-continued

|  |  | Example | Comparative Example | | | | | |
|---|---|---|---|---|---|---|---|---|
| Phase | Ingredient | 1 | 1 | 2 | 3 | 4 | 5 | 6 |
|  | Iron oxides (and) disodium stearoyl glutamate (and) aluminum hydroxide (NAI-C33-8001-10/Miyoshi Kasei) | 0.01 | 0.01 | 0.01 | 0.01 | 0.01 | 0.01 | 0.01 |
| D | Water | 35.00 | 35.00 | 35.00 | 35.00 | 35.00 | 35.00 | 35.00 |
| E | Alcohol | 10.00 | 10.00 | 10.00 | 10.00 | 10.00 | 10.00 | 10.00 |
|  | TOTAL | 100.00 | 100.00 | 100.00 | 100.00 | 100.00 | 100.00 | 100.00 |
|  | LASTING (n = 5) | ○ | ○ | X | X | X | X | X |
|  | MOISTURE (n = 5) | ○ | X | ○ | X | ○ | ○ | ○ |

Liquid Foundation Example

Examples 2 and 3 and Comparative Examples 7 and 8

The liquid foundation compositions according to Examples 2 and 3 and Comparative Examples 7 and 8 shown in Table 2 were prepared by mixing the ingredients shown in Table 2 in the same manner as described in the "Makeup Base Example" above. The numerical values for the amounts of the ingredients shown in Table 2 are all based on "% by weight" as active raw materials.

Moisturizing effects were evaluated during and after the application. The criteria of the evaluation are as follows:
O: Perception of moisturizing feeling
X: Lack of moisturizing feeling "Long-lasting" effects were evaluated by applying a powder foundation onto the makeup base compositions for Example 1 and Comparative Examples 1 to 6, or applying nothing onto the liquid foundation compositions for Examples 2 and 3 and Comparative Examples 7 and 8, and then checking the shine of the face after three hours of the application. The criteria of the evaluation are as follows:
O: Good lasting of foundation
X: Bad lasting of foundation

TABLE 2

|  |  | Example | | Comparative Example | |
|---|---|---|---|---|---|
| Phase | Ingredient | 2 | 3 | 7 | 8 |
| A1 | PEG-10 Dimethicone | 3.00 | 3.00 | 3.00 | 3.00 |
|  | BIS-PEG/PPG-14/14 Dimethicone (and) dimethicone | 1.00 | 1.00 | 1.00 | 1.00 |
|  | Dimethicone | qs 100 | qs 100 | qs 100 | qs 100 |
| A2 | Diisopropyl sebacate (Dub Dis by Stearinerie Dubois) | 2.00 | — | — | 2.00 |
|  | Isopropyl lauroyl sarcosinate (Eldew SL-205 by Ajinomoto) | — | 2.00 | — | — |
|  | Dipentaerythrityl tetrahydroxystearate/tetraisostearate (SalacosS 168 EV by Nisshin Oillio) | 0.30 | 0.30 | — | 0.30 |
|  | Ethylhexyl methoxycinnamate (Uvinul MC 80 by BASF) | — | — | — | 8.00 |
| A3 | Trimethylsiloxysilicate (SR 1000 MQ Resin by Momentive Performance Materials) | 5.00 | 5.00 | 5.00 | 5.00 |
| A4 | Disteardimonium hectorite | 1.00 | 1.00 | 1.00 | 1.00 |
| B | Silica silylate (Dow Corning VM-2270 Aerogel Fine Particles) | 0.10 | 1.00 | 0.10 | 0.10 |
|  | Acrylonitrile/methyl methacrylate/vinylidene chloride copolymer (Expancel 551 DE 40 D42 by Akzo Nobel) | 0.10 | 0.50 | 0.10 | — |
|  | Perlite (Perlite-M SZ12 by Miyoshi Kasei) | 1.00 | 3.00 | 1.00 | 1.00 |
|  | HDI/trimethylol hexyllactone crosspolymer (Plastic Powder D 400 by Toshiki Pigment) | 0.50 | 3.00 | 0.50 | 0.50 |
| C | Titanium dioxide (and) aluminum hydroxide (and) dimethicone (and) hydrogen dimethicone | 5.00 | 5.00 | 5.00 | 5.00 |
|  | Titanium dioxide (and) disodium stearoyl glutamate (and) aluminum hydroxide (NAI-TAO-77891/Miyoshi Kasei) | 10.72 | 10.72 | 10.72 | 10.72 |
|  | Iron oxides (and) disodium stearoyl glutamate (and) aluminum hydroxide (NAI-C33-7001-10/Miyoshi Kasei) | 0.11 | 0.11 | 0.11 | 0.11 |
|  | Iron oxides (and) disodium stearoyl glutamate (and) aluminum hydroxide (NAI-C33-9001-10/Miyoshi Kasei) | 2.12 | 2.12 | 2.12 | 2.12 |
|  | Iron oxides (and) disodium stearoyl glutamate (and) aluminum hydroxide (NAI-C33-8001-10/Miyoshi Kasei) | 0.39 | 0.39 | 0.39 | 0.39 |
| D | Water | 30.00 | 30.00 | 30.00 | 30.00 |
| E | Alcohol | 7.00 | 7.00 | 7.00 | 7.00 |
|  | TOTAL | 100.00 | 100.00 | 100.00 | 100.00 |
|  | LONG-LASTING (n = 5) | ○ | ○ | ○ | X |
|  | MOISTURIZING (n = 5) | ○ | ○ | X | ○ |

[Evaluation]

The compositions according to Examples 1 to 3 were applied onto half of the face of a user in the appropriate amount, while those according to Comparative Examples 1 to 8 were applied onto the other half of the face of the user in the same amount. After that, the compositions were spread with the fingers to form a cosmetic film. Five users participated in the evaluation test.

The results of the evaluations are shown in Tables 1 and 2.

Regarding the makeup base compositions (Table 1), the composition according to Example 1, which comprised at least one moisturizer (dipentaerythrityl tetrahydroxystearate/tetraisostearate), a film-forming polymer (trimethylsiloxysilicate) and a filler combination of the present invention (silica silylate, perlite, HDI/trimethylol hexyllactone crosspolymer, and lauryl methacrylate/glycol dimethacrylate crosspolymer), was able to provide a moisturizing feeling and had "long-lasting" effects.

On the other hand, the composition according to Comparative Example 1, which comprised the film-forming polymer and the filler combination of the present invention but did not comprise moisturizers, was not able to provide a moisturizing feeling.

The composition according to Comparative Example 2, which comprised the moisturizer and the filler combination of the present invention but did not comprise the film-forming polymer, did not have "long-lasting" effects.

The compositions according to Comparative Examples 3 to 6 comprised the moisturizer and the film-forming polymer but did not comprise one of the essential fillers of the present invention. These compositions did not have "long-lasting" effects.

This demonstrates that it is necessary to add not only a film-forming polymer but also all of the essential fillers for the present invention (i.e., hydrophobic silica, perlite, urethane polymer powder, and acrylic polymer powder) to a cosmetic composition comprising a moisturizer in order to have "long-lasting" effects while providing a moisturizing feeling.

This is also supported in the results obtained by using the liquid foundation compositions (Table 2).

The invention claimed is:

1. A method for improving long-lasting effects without creating any dry feeling in a cosmetic composition, comprising adding to the cosmetic composition at least one film-forming polymer and a combination of the following fillers:
   (a) hydrophobic silica,
   (b) perlite,
   (c) urethane polymer powder, and
   (d) acrylic polymer powder,
   wherein the urethane polymer powder is a hexamethylene diisocyanate (HDI)/trimethylol hexyllactone crosspolymer,
   wherein the cosmetic composition comprises at least one moisturizer,
   wherein the at least one moisturizer is a combination of:
      (A) a polyol ester formed between (i) a polyol selected from pentaerythritol, erythritol, di-pentaerythritol, trimethylolpropane, di-trimethylolpropane, glycerol, diglycerol, polyglycerols, or sucrose, and (ii) hydroxystearic acid and isostearic acid; and
      (B2) a $C_6$-$C_{22}$ N-acylamino acid ester of the following formula:

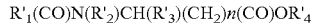

in which:
   the $R'_1(CO)$ portion is an acyl group of an acid selected from capric acid, lauric acid, myristic acid, palmitic acid, stearic acid, behenic acid, linoleic acid, linolenic acid, oleic acid, isostearic acid, 2-ethylhexanoic acid, coconut oil fatty acids, or palm kernel oil fatty acids;
   the $N(R'_2)CH(R'_3)(CH_2)_n(CO)$ portion is an amino acid selected from glycine, alanine, valine, leucine, isoleucine, serine, threonine, proline, hydroxyproline, β-alanine, aminobutyric acid, aminocaproic acid, sarcosine, or N-methyl-β-alanine; and
   the $OR'_4$ portion is obtained from alcohols selected from methanol, ethanol, propanol, isopropanol, butanol, tert-butanol, isobutanol, 3-methyl-1-butanol, 2-methyl-1-butanol, fusel oil, pentanol, hexanol, cyclohexanol, octanol, 2-ethylhexanol, decanol, lauryl alcohol, myristyl alcohol, cetyl alcohol, cetostearyl alcohol, stearyl alcohol, oleyl alcohol, behenyl alcohol, jojoba alcohol, 2-hexadecyl alcohol, 2-octyldodecanol, or isostearyl alcohol,
wherein the total amount of moisturizers ranges from about 0.05% to about 10% by weight, relative to the total weight of the composition,
wherein the total amount of film-forming polymers ranges from about 1% to about 10% by weight, relative to the total weight of the composition, and
wherein each of fillers (a)-(d) is present in an amount ranging from about 0.05% to about 5.0% by weight, relative to the total weight of the composition.

2. The method according to claim 1, wherein the at least one film-forming polymer is chosen from silicone resins.

3. The method according to claim 1, wherein the at least one hydrophobic silica is chosen from silica particles modified at the surface by silylation.

4. The method according to claim 1, wherein the at least one acrylic polymer powder is chosen from crosspolymer or copolymer powders.

5. The method according to claim 1, wherein the at least one acrylic polymer powder is chosen from lauryl methacrylate/glycol dimethacrylate crosspolymer or acrylonitrile/methacrylate/vinylidene chloride copolymer.

6. The method according to claim 1, wherein the composition further comprises at least one UV filter.

7. The method according to claim 1, wherein the composition is a makeup base or a liquid foundation.

8. The method according to claim 1, wherein the composition is in the form of an emulsion.

* * * * *